United States Patent
Nose et al.

(10) Patent No.: US 8,975,455 B2
(45) Date of Patent: Mar. 10, 2015

(54) METHOD FOR PRODUCING PENTAFLUOROETHANE

(75) Inventors: Masatoshi Nose, Osaka (JP); Kazuhiro Takahashi, Osaka (JP); Takashi Shibanuma, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 379 days.

(21) Appl. No.: 12/747,696

(22) PCT Filed: Nov. 12, 2008

(86) PCT No.: PCT/JP2008/070548
§ 371 (c)(1),
(2), (4) Date: Jun. 11, 2010

(87) PCT Pub. No.: WO2009/078234
PCT Pub. Date: Jun. 25, 2009

(65) Prior Publication Data
US 2010/0268002 A1   Oct. 21, 2010

(30) Foreign Application Priority Data

Dec. 14, 2007 (JP) .................................. 2007-322883
May 22, 2008 (JP) .................................. 2008-134424

(51) Int. Cl.
*C07C 19/08* (2006.01)
*C07C 17/21* (2006.01)
(52) U.S. Cl.
CPC ........................................ *C07C 17/21* (2013.01)
USPC ........................................................ 570/168
(58) Field of Classification Search
None
See application file for complete search history.

(56) References Cited

U.S. PATENT DOCUMENTS

| 5,545,778 | A | 8/1996 | Tung et al. |
| 5,849,160 | A | 12/1998 | Homoto et al. |
| 5,849,658 | A | 12/1998 | Shibanuma et al. |
| 5,932,776 | A | 8/1999 | Cheminal et al. |
| 6,433,233 | B1 | 8/2002 | Kanemura et al. |
| 6,455,745 | B1 * | 9/2002 | Takahashi et al. ............ 570/166 |

(Continued)

FOREIGN PATENT DOCUMENTS

| JP | 5-97725 A | 4/1993 |
| JP | 5-146680 A | 6/1993 |
| JP | 6-247884 A | 9/1994 |

(Continued)

OTHER PUBLICATIONS

Interantional Search Report mailed Jan. 20, 2009 in Application No. PCT/JP2008/070548.

*Primary Examiner* — Clinton Brooks
(74) *Attorney, Agent, or Firm* — Birch, Stewart, Kolasch & Birch, LLP

(57) ABSTRACT

The present invention aims in a method wherein tetrachloroethylene (PCE) is reacted with HF in a gas phase in the presence of a catalyst to obtain pentafluoroethane (HFC-125), to reduce production of undesirable by-products and maintain a catalytic activity at a high level over a long period of time while achieving a high conversion ratio of PCE and suppressing deterioration of the catalyst.

In a method for producing pentafluoroethane wherein tetrachloroethylene is reacted with HF in a gas phase in the presence of a catalyst to obtain pentafluoroethane, characterized in that chromium oxyfluoride is disposed in a reactor as the catalyst, and oxygen is fed into the reactor together with tetrachloroethylene and HF, at a amount of 0.4-1.8% by mole with respect to tetrachloroethylene.

4 Claims, 1 Drawing Sheet

(56) References Cited

U.S. PATENT DOCUMENTS

| | | |
|---|---|---|
| 2004/0049088 A1 | 3/2004 | Lacroix et al. |
| 2007/0129581 A1 | 6/2007 | Boussand et al. |

FOREIGN PATENT DOCUMENTS

| | | |
|---|---|---|
| JP | 8-301800 A | 11/1996 |
| JP | 10-505341 A | 5/1998 |
| JP | 10-180104 A | 7/1998 |
| JP | 11-171806 A | 6/1999 |
| JP | 2003-513059 A | 4/2003 |
| WO | WO 95/16654 A1 | 6/1995 |
| WO | WO 96/06062 A1 | 2/1996 |
| WO | WO 96/11176 A1 | 4/1996 |
| WO | WO 01/32592 A1 | 5/2001 |

* cited by examiner

METHOD FOR PRODUCING PENTAFLUOROETHANE

TECHNICAL FIELD

The present invention relates to a method for producing pentafluoroethane (hereinafter, also referred to as HFC-125), and more particularly to a method for producing HFC-125 from tetrachloroethylene (or perchloroethylene, hereinafter, also referred to as PCE).

BACKGROUND ART

Pentafluoroethane (HFC-125) is an important substance as a substitute for CFC or HCFC which causes ozone layer destruction, and is widely used, for example, as refrigerants, mixed refrigerants (R-410A, R-407C, R-404A), blowing agents and propellants.

A number of methods for producing HFC-125 have been known. Among them, a method in which tetrachloroethylene (PCE) is used as a starting material and fluorinated in a single-stage gas phase in the presence of a catalyst to obtain HFC-125 is practical as a commercially advantageous production method.

It is known that in such a fluorination reaction, oxygen is added to the reaction system so as to suppress deterioration of the catalyst (see Patent Citations 1 to 4). A conventional production method will be described in more detail below.

Patent Citation 1 describes that various catalysts including oxides, halides and oxyhalides of chromium can be used, and a small amount of oxygen is preferably fed so as to maintain a catalytic activity of chromium oxide, and also describes that the feeding amount of oxygen is preferably about 0.01-30% by mole, more preferably about 0.05-20% by mole, and still more preferably about 0.1-10% by mole, with respect to the total organic substances to be fed into a reactor.

Patent Citation 2 describes that a mixed catalyst of oxides, halides and/or oxyhalides of nickel and chromium supported on an aluminum fluoride carrier is used, and it is well-advised to introduce oxygen at a low concentration together with reactants under conditions where the catalyst can be contaminated, and also describes that the feeding amount of oxygen may be about 0.02-5% by mole with respect to the organic reactants.

Patent Citation 3 describes that various catalysts including oxides, halides and oxyhalides of chromium can be used, and it is well-advised to introduce a small amount of oxygen together with reactive species, and also describes that the feeding amount of oxygen may be 0.02-1% by mole with respect to a gas mixture to be introduced into a reactor. Since Patent Citation 3 describes that a HF/PCE molar ratio is not smaller than 20, the feeding amount of oxygen is at least 0.42-21% by mole with respect to PCE.

Patent Citation 4 suggests use of a nonchromium-based catalyst, because a conventionally used chromium oxide-based catalyst brings about by-products when oxygen is added, and thus the objective substance cannot be selectively obtained, and also it is difficult to maintain a catalytic activity for a long time. Patent Citation 4 describes that oxygen is added preferably at an amount of 0.1-10% by volume with respect to PCE so as to maintain a catalytic activity of the proposed nonchromium-based catalyst, and also describes Examples and Comparative Examples in which oxygen is added at an amount of 2.5% by volume, 4% by volume and 5% by volume with respect to PCE. Furthermore, according to Patent Citation 4, in Examples where PCE was fluorinated for a long time, HFC-125 was scarcely produced, and the main product was HCFC-122 or HCFC-123. Therefore, Patent Citation 4 does not substantially describe a method in which HFC-125 is produced from PCE as a raw material in a single-stage gas phase.

Patent Citation 1: U.S. Pat. No. 5,545,778 A
Patent Citation 2: JP 6-247884 A
Patent Citation 3: US 2007/0129581 A1
Patent Citation 4: JP 5-97725 A
Patent Citation 5: WO 96/11176 A1
Patent Citation 6: JP 5-146680 A
Patent Citation 7: JP 11-171806 A

DISCLOSURE OF INVENTION

Technical Problem

A conventional production method using a chromium-based catalyst had such a problem that, addition of oxygen to the reaction system can suppress deterioration of the catalyst, and, however, brings about a large amount of undesirable by-products and also decreases a catalytic activity.

More specifically, oxygen reacts with hydrogen chloride, which is produced by the fluorination reaction, to produce water and chorine (oxychlorination: $O_2 + 4HCl \rightarrow 2H_2O + 2Cl_2$), and this chlorine may cause chlorinated by-products, for example, CFC-115 ($CClF_2CF_3$), CFC-114a ($CCl_2FCF_3$) and CFC-113a ($CCl_3CF_3$). Inter alia, CFC-115 is inconvenient since its boiling point is close to that of HFC-125 as the objective substance, so that a process other than a conventional distillation, e.g. an extractive distillation, must be used to remove CFC-115. Also with the addition of oxygen, oxygen may cause HFC-23 ($CHF_3$) and $CO_2$ as oxygen-decomposed by-products.

Furthermore with the addition of oxygen, since the activity of the catalyst decreases, a conversion ratio of PCE decreases and a large amount of the unreacted PCE remains. The reaction mixture (gas mixture) contains PCE and is therefore separated into a HF phase (upper phase) and an organic substance phase (lower phase) when condensed. Then, in order to reuse unreacted raw material and intermediates, which can produce and the objective substance, as a raw material in a continuous operation, the two phases separated as above must be independently recycled, and needs complicated steps. Specifically, in Examples of Patent Citation 1, while an amorphous $Cr_2O_3$ catalyst was used, oxygen was added to the reaction system at an amount of 2% by mole with respect to PCT (Example 1, raw material: PCE), or at an amount of 1% by mole with respect to the organic substances (Examples 2-4, raw material: PCE (30% by weight) and HCFC-123 ($CCl_2HCF_3$) (70% by weight), therefore at an amount of about 3.5% by mole with respect to PCE), and then the PCE conversion ratio was about 67-82% and a large amount of PCE remained in the reaction mixture. In order to avoid phase separation described above, it may be considered to separate PCE from the reaction mixture (see Patent Citation 5). However, there arises a problem of complex process and cost increase.

The present invention aims to provide a method for producing HFC-125 wherein PCE is reacted with HF in a gas phase in the presence of a catalyst to obtain HFC-125, which can reduce production of undesirable by-products and maintain a catalytic activity at a high level over a long period of time while achieving a high conversion ratio of PCE and suppressing deterioration of the catalyst.

Technical Solution

The present inventors have intensively studied about the catalyst to be used for a fluorination reaction and the additive amount of oxygen, and thus the present invention has been completed.

According to one aspect of the present invention, there is provided a method for producing pentafluoroethane wherein tetrachloroethylene (PCE) is reacted with HF in a gas phase in the presence of a catalyst (hereinafter, the reaction is also referred to as a "fluorination reaction") to obtain pentafluoroethane (HFC-125), characterized in that chromium oxyfluoride is disposed in a reactor as the catalyst, and oxygen is fed into the reactor together with tetrachloroethylene and HF, at a amount of 0.4-1.8% by mole with respect to tetrachloroethylene.

In the present invention, chromium oxyfluoride is particularly used among other various fluorination catalysts, and a certain range at a very low level (i.e. 0.4-1.8% by mole with respect to PCE) is selected for the feeding amount of oxygen, and the present inventors have found that these produce significant effects being capable of reducing production of undesirable by-products and maintaining a catalytic activity at a high level over a long period of time while achieving a high conversion ratio of PCE and suppressing deterioration of the catalyst. If the feeding amount of oxygen with respect to PCE is less than 0.4% by mole, the conversion ratio of PCE decreases with the passage of reaction time, and a deterioration rate of the catalyst increases. Then, if the feeding amount of oxygen with respect to PCE is more than 1.8% by mole, the catalytic activity decreases, the conversion ratio of PCE decreases, and the produced amount of undesirable by-products increases. Such a combination of the fluorination catalyst and the feeding amount of oxygen has never been known, and it is unprecedented and original findings of the present inventors that the significant effects can be produced by actually applying the feeding amount of oxygen in a range at such a low level. According to the present invention, it becomes possible to maintain a selectivity of HFC-125 and a conversion ratio of PCE at high levels over a long period of time.

In the production method of the present invention, it is preferred that tetrachloroethylene and HF are fed into the reactor at a molar ratio of HF to tetrachloroethylene of not smaller than 20.

The fluorination reaction can be carried out, for example, at a temperature of about 310-380° C. Thus, it is possible to allow the reaction of producing HFC-125 from PCE to proceed efficiently in a single-stage gas phase. However, the present invention is not limited thereto, and any appropriate reaction conditions (including temperature, pressure and contact time) can be applied.

In one embodiment of the present invention, a fraction comprising pentafluoroethane and hydrogen chloride may be separated from a reaction mixture which has been obtained from the reactor, and all of a remainder thereof may be returned to the reactor. According to the present invention, a very high conversion ratio of PCE can be achieved so that the reaction mixture is not phase separated, thus it is possible to separate the reaction mixture simply and easily into a fraction comprising pentafluoroethane and hydrogen chloride and other fractions to be recycled by, for example, distillation operation.

ADVANTAGEOUS EFFECTS

According to the present invention, it becomes possible by using chromium oxyfluoride particularly among other various fluorination catalysts, and selecting a certain range at a very low level (i.e. 0.4-1.8% by mole with respect to PCE) for the feeding amount of oxygen, to reduce production of undesirable by-products and maintain a catalytic activity at a high level over a long period of time while achieving a high conversion ratio of PCE and suppressing deterioration of the catalyst. According to the present invention, it becomes possible to maintain a selectivity of HFC-125 and a conversion ratio of PCE at high levels over a long period of time.

EXPLANATION OF REFERENCE 1, 5, 9, 11, 13, 17, 19: Lines
3: Reactor
7: Distillation column
15: Condenser

BEST MODE FOR CARRYING OUT THE INVENTION

The method for producing HFC-125 in one embodiment of the present invention will be described in detail below with reference to the accompanying drawings.

First, a chromium oxyfluoride catalyst is prepared as a catalyst for the fluorination reaction. Chromium oxyfluoride (which may be also called as fluorochromium oxide) can be obtained by fluorinating chromium oxide with HF (generally, anhydrous hydrogen fluoride). For example, chromium oxyfluoride can be prepared by the method described in Patent Citation 6. This chromium oxyfluoride catalyst is preferably in the amorphous (noncrystalline) state, and an average valence number of chromium is from +3.5 to +5.0. The amorphous state can be recognized by, for example, the fact that a measured X-ray diffraction shows no diffraction peak attributed to a specific crystal structure. The average valence number of chromium can be determined by composition analysis or magnetic susceptibility measurement, and is more preferably from +3.6 to 4.8, and still more preferably from 4.0 to 4.5. This chromium oxyfluoride catalyst may have a surface area (measured by the BET method) of, for example, about 25-130 $m^2/g$. To such a catalyst, any appropriate metallic element, for example, at least one metallic element selected from the group consisting of indium, gallium, cobalt, nickel, zinc and aluminum may be added; and at least one metallic element selected from the group consisting of cadmium, magnesium and titanium may be further added in addition to the above metallic element. Such a catalyst includes, for example, a chromium oxyfluoride catalyst as described in Patent Citation 7.

Figure 1:
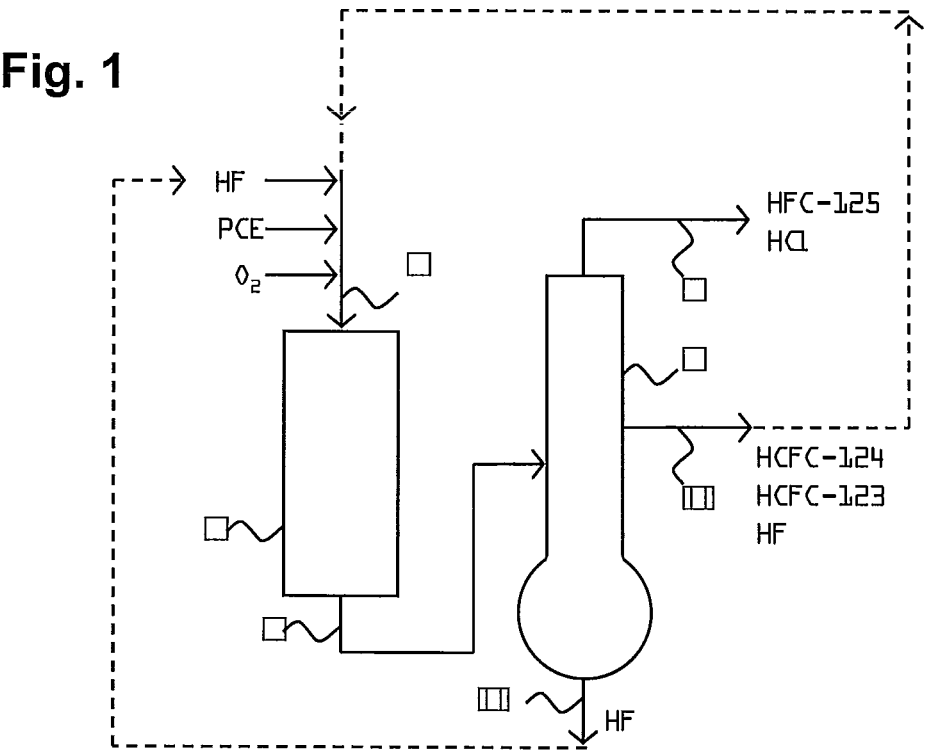
FIG. 1 is a schematic process diagram for explaining a method for producing HFC-125 in one embodiment of the present invention.

Referring to FIG. 1, this chromium oxyfluoride catalyst is disposed in a reactor 3. The reactor 3 is generally packed with the catalyst. Any appropriate reactor may be used as the reactor 3. For example, the reactor may be an adiabatic reactor, or a multitubular reactor in which heat is removed by using a heat medium. The reactor 3 is preferably composed of materials, at least the inner surface of which is made of a material having a resistance to a corrosive action of hydrogen fluoride, for example, HASTELLOY, INCONEL and MONEL.

Then, tetrachloroethylene (PCE), hydrogen fluoride (HF) and oxygen ($O_2$) are fed into the reactor 3, in which the chromium oxyfluoride catalyst is disposed, in the gas state through a line 1. HF is usually fed in the form of an anhydrous hydrogen fluoride. Oxygen may be fed either in a form of oxygen alone or a form of an oxygen containing gas (for example, air). PCE, HF and oxygen may be fed into the reactor 3, independently.

PCE and HF are fed so that a molar ratio of HF to PCE (HF/PCE) is preferably not smaller than about 20, and more preferably about 20-30.

The feeding amount of oxygen is 0.4-1.8% by mole, and preferably 0.4-1.5% by mole, with respect to PCE.

In this reactor 3, PCE ($CCl_2=CCl_2$) reacts with HF in a gas phase in the presence of a chromium oxyfluoride catalyst (fluorination reaction) to produce HFC-125 ($CF_2HCF_3$) as the objective substance via HCFC-122 ($CCl_2HCClF_2$), HCFC-123 ($CCl_2HCF_3$) and HCFC-124 ($CClFHCF_3$).

The reaction temperature is, for example, about 310-380° C., and preferably about 320-360° C. The reaction pressure is, for example, about 0.1 MPa to 2.0 MPa, and preferably under pressure of, for example, about 0.3-0.4 MPa. However, the present embodiment is not limited thereto and, for example, the reaction may be carried out under normal pressure. Herein, the reaction temperature and the reaction pressure mean a temperature and a pressure in the reactor 3.

The contact time between the catalyst and the raw material gas (reactant) fed into the reactor 3 is, for example, about 6-30 seconds, and preferably about 8-15 seconds. In the present description, the "contact time" means a time required for the raw material gas fed into the reactor to pass through the catalyst portion (catalyst bed) in the standard state (0° C., 1 atm (=0.1013 MPa)) on the assumption that the void ratio of the catalyst portion (catalyst bed) in the reactor 3 is 100%.

The reaction mixture (gas mixture) after the fluorination reaction is obtained from the reactor 3 through a line 5. In the present embodiment, the fluorination reaction is continuously carried out in a single-stage gas phase.

The reaction mixture thus obtained comprises HFC-125 as the objective substance and hydrogen chloride (HCl) as a by-product of the fluorination reaction, and may further contain the unreacted HF, HCFC-124 and HCFC-123 as intermediates, and so on.

The fluorination reaction has a high conversion ratio of PCE, preferably it is about 95% or more. Therefore, PCE is scarcely contained in the reaction mixture obtained in the present embodiment.

Although the selectivity varies depending on the reaction conditions, the fluorination reaction shows a high selectivity of HFC-125 as the objective substance, so that the present process is suited for a method for producing HFC-125.

During the fluorination reaction, products other than HFC-125 may be produced. Among the products other than HFC-125, products which are able to produce HFC-125 by further reacting with HF are referred to as an "intermediates", while products which are not able to produce HFC-125 by further reacting with HF are referred to as "undesirable by-products", herein. Examples of the intermediates having a possibility to be produced include HCFC-124 ($CClFHCF_3$), HCFC-124a ($CClF_2CF_2H$), HCFC-123 ($CCl_2HCF_3$), HCFC-123a ($CClF-HCClF_2$), HCFC-122 ($CCl_2HCClF_2$), CFC-1111 ($CCl_2CClF$) and CFC-1112a ($CCl_2CF_2$). Examples of the undesirable by-products having a possibility to be produced include HCFC-133a ($CClH_2CF_3$), HFC-134a ($CFH_2CF_3$), CFC-115 ($CClF_2CF_3$), CFC-114a ($CCl_2FCF_3$), CFC-113a ($CCl_3CF_3$), HFC-23 ($CHF_3$) and $CO_2$.

The products other than HFC-125, which are contained in the reaction mixture obtained in the present embodiment, are mainly intermediates, particularly HCFC-124 and HCFC-123. The sum of selectivity of the objective substance and those of the intermediates is very high and, particularly, the sum of selectivities of HFC-125, HCFC-124 and HCFC-123 can be preferably about 95% by mole or more.

On the other hand, the undesirable by-products are scarcely contained in the reaction mixture obtained in the present embodiment. The sum of selectivities of the undesirable by-products can be preferably less than about 5% by mole.

Since the reaction mixture thus obtained scarcely contains PCE as described above, it does not cause phase separation (liquid-liquid separation), and therefore can be directly fed into a distillation column 7.

In the distillation column 7, the reaction mixture is subjected to a distillation operation under appropriate conditions and a first fraction is separated from a column top through a line 9, and the first fraction is substantially composed of HFC-125 and HCl as low-boiling point components. The resultant fraction is, for example, washed with water to remove HCl, and thus HFC-125 can be obtained (not shown). This first fraction may contain, in addition to HFC-125 and HCl, other low-boiling point components which could exist, for example, oxygen supplied into the reactor 3 as well as HFC-134a, HFC-23, $CO_2$ and CFC-115 as by-products. However, the total amount of these other low-boiling point components contained in the first fraction is a small amount, since the amount of oxygen to be fed is smaller than that in the conventional method, and thereby the amount of by-products produced, which depends on the amount of oxygen, is also small. These other low-boiling point components can be easily separated by distillation in the post-process, as required, except for CFC-115, and also the amounts of these low-boiling point components and oxygen, which must be separated, are small, so that energy cost required to distillation and loss in HFC-125 caused during distillation can be decreased. Although CFC-115 is produced in a small amount compared with that in the conventional method, it may be removed by extractive distillation, if required.

On the other hand, a second fraction is obtained from the column bottom of the distillation column 7 through a line 13, and the second fraction is substantially composed of HF as a high-boiling point component. A third fraction is obtained from a middle stage of the distillation column 7 through a line 11, and the third fraction is substantially composed of HCFC-124, HCFC-123 and HF. The second and third fractions correspond to the remainder obtained after separating the first fraction comprising HFC-125 and HCl (low-boiling point component fraction) from the reaction mixture, and all of the remainder may be returned to the reactor 3 (shown by dotted lines in the drawing). Thus, the unreacted HF, HCFC-124 and HCFC-123 can be reused for the fluorination reaction. At this time, the second and/or third fractions may additionally contain CFC-113a, CFC-114a and HCFC-133a, and these components are returned together to the reactor 3. It has been found by the present inventors that, while recycling, CFC-113a and CFC-114a are fluorinated into CFC-115 in due course, and HCFC-133a is fluorinated into HFC-134a in due course, and they can be separated as the first fraction from the column top of the distillation column 7 through the line 9, and are not concentrated into the reaction mixture. Therefore, all of the remainder obtained after separating the first fraction from the reaction mixture, that is, all of the second and third fractions can be returned to the reactor 3.

Figure 2:
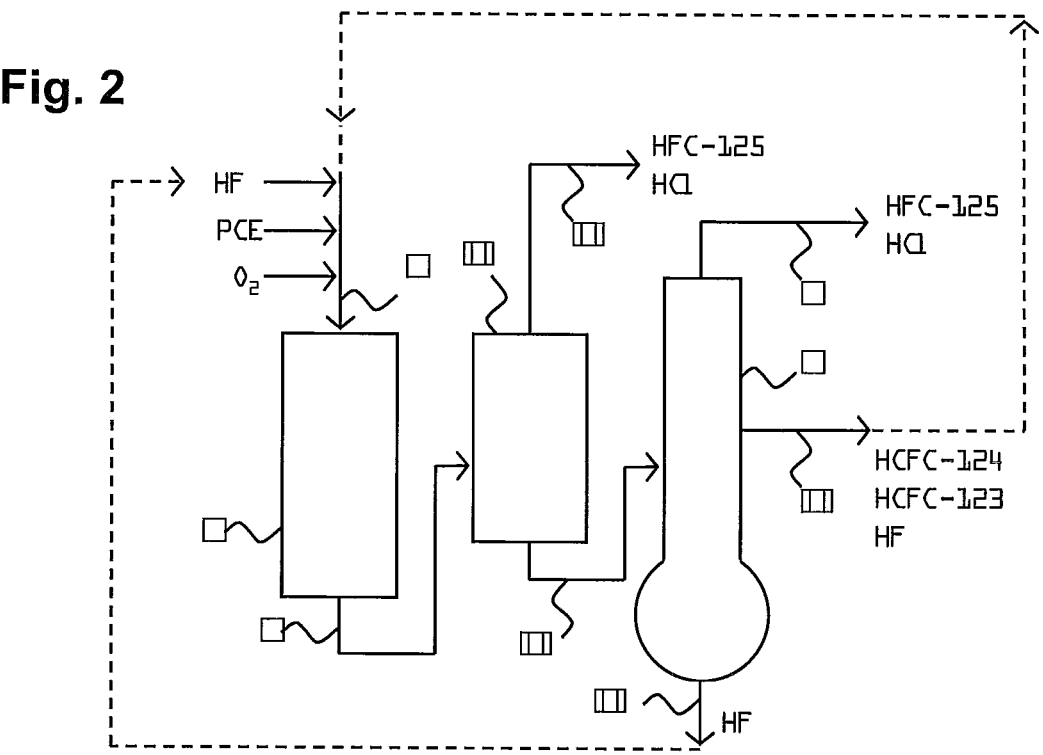
FIG. 2 is a schematic process diagram for explaining a modification example of FIG. 1.

While one embodiment of the present invention has been described, but the present invention is not limited thereto and various modifications of embodiments can be made. For example, as shown in FIG. 2, a condenser 15 is provided between a reactor 3 and a distillation column 7, the reaction mixture (gas mixture) obtained from the reactor 3 through a line 5 may be condensed in the condenser 15 to be separated into a non-condensable fraction and a condensable fraction. The non-condensable fraction is substantially composed of HFC-125 and HCl as low-boiling point components and is separated from the reaction mixture through a line 17. The condensable fraction as the remainder is fed into the distillation column 7 through a line 19, where the condensable fraction is subjected to the distillation operation described above. Thus, HFC-125 and HCl can be removed to some extent prior to the distillation operation, so that load on the distillation column 7 can be reduced.

EXAMPLES

Example 1

A tubular reactor made of HASTELLOY and having an inner diameter of 20 mm and a length of 1 m was packed with 69.0 g of a chromium oxyfluoride catalyst (fluorine content: about 15.0% by weight) which had been obtained by subjecting chromium oxide to a fluorination treatment. This reactor was maintained at 0.32 MPa and 350° C., and HF (anhydrous hydrogen fluoride) was fed into the reactor in the amount of 357 cc/min. One hour after the beginning of feeding, PCE (substantially pure tetrachloroethylene) was fed into the reactor in the amount of 17 cc/min and, at the same time, oxygen ($O_2$) was fed into the reactor in the amount of 0.136 cc/min. Therefore, the molar ratio of HF to PCE (HF/PCE) was 21, and the feeding amount of oxygen with respect to PCE was 0.8% by mole. The starting point of feeding of HF and oxygen was regarded as start of the reaction. The contact time was 11.1 seconds. The reaction mixture flowing out from the reactor was analyzed using an online gas chromatograph. The results of analysis performed 71 hours and 1,093 hours after the start of the reaction are shown in Table 1.

Example 2

The same procedures were conducted as in Example 1, except that the packed amount of the catalyst was 70.0 g, the tubular reactor was maintained at about 0.25 MPa and 350° C., the feeding amount of HF was 405 cc/min, the feeding amount of PCE was 15 cc/min, and the feeding amount of oxygen was 0.225 cc/min, so that a molar ratio of HF to PCE was 27 and the feeding amount of oxygen with respect to PCE was 1.5% by mole, and the contact time was 10 seconds. The results of analysis performed 96 hours and 2,318 hours after the start of the reaction are shown in Table 1.

Example 3

The same procedures were conducted as in Example 2, except that the packed amount of the catalyst was 63.0 g, the tubular reactor was maintained at 0.1 MPa (atmospheric pressure) and 359° C., the feeding amount of oxygen was 0.06 cc/min, so that the feeding amount of oxygen with respect to PCE was 0.4% by mole, and the contact time was 9 seconds. The results of analysis performed 70 hours and 1,460 hours after the start of the reaction are shown in Table 1.

Example 4

The same procedures were conducted as in Example 2, except that the packed amount of the catalyst was 77.0 g, the tubular reactor was maintained at 0.25 MPa and 329° C., and the feeding amount of oxygen was 0.09 cc/min, so that the feeding amount of oxygen with respect to PCE was 0.6% by mole, and the contact time was 11 seconds. The results of analysis performed 94 hours and 779 hours after the start of the reaction are shown in Table 1.

Example 5

Assuming that HCFC-123 and HCFC-124 as intermediates were recycled, a test was carried out. In this Example, not only PCE, but PCE, HCFC-123 and HCFC-124 were used as organic substances for the raw materials, and a PCE/HCFC-124/HCFC-123 ratio was about 62/28/10 (% by mole).

The same procedures were conducted as in Example 1, except that the packed amount of the catalyst was 76.3 g, the tubular reactor was maintained at about 0.16 MPa and 350° C., the feeding amount of HF was 432 cc/min, HCFC-124 and HCFC-123 were fed simultaneously with PCE, the feeding amount of PCE was 16 cc/min, the feeding amount of HCFC-124 was 7.2 cc/min, the feeding amount of HCFC-123 was 2.6 cc/min, and the feeding amount of oxygen was 0.16 cc/min, so that the molar ratio of HF to PCE was 27 (a molar ratio of HF to the total organic substances for the raw materials was about 16.7) and the feeding amount of oxygen with respect to PCE was 1.0% by mole, and the contact time was 10 seconds. The results of analysis performed 72 hours and 1,087 hours after the start of the reaction are shown in Table 1.

TABLE 1

| | | | Example 1 | | Example 2 | | Example 3 | | Example 4 | | Example 5 | |
|---|---|---|---|---|---|---|---|---|---|---|---|---|
| After start of reaction (hours) | | | 71 | 1093 | 96 | 2318 | 70 | 1460 | 94 | 779 | 72 | 1087 |
| Conversion ratio of PCE (%) | | | 100 | 99.9 | 100 | 99.9 | 100 | 99.0 | 99.8 | 99.2 | 100 | 100 |
| Selectivity (% by mole) | Objective substance | HFC-125 | 61.9 | 61.7 | 59.2 | 58.9 | 74.4 | 71.8 | 30.2 | 29.5 | 60.6 | 60.5 |
| | Intermediates | HCFC-124 HCFC-124a | 24.8 | 24.9 | 25.8 | 26.0 | 14.9 | 17 | 32.5 | 32.8 | 23.5 | 23.6 |
| | | HCFC-123 HCFC-123a | 9.1 | 9.2 | 10.3 | 10.4 | 8.5 | 8.7 | 33.1 | 33.4 | 12.7 | 12.7 |
| | | HCFC-122 | 0.1 | 0.1 | 0.1 | 0.1 | 0 | 0.1 | 0.3 | 0.3 | 0 | 0 |
| | | CFC-1111 | 0.1 | 0.1 | 0.1 | 0.1 | 0 | 0.1 | 1.0 | 1.0 | 0 | 0 |
| | | CFC-1112a | 0 | 0 | 0 | 0 | 0 | 0 | 0.3 | 0.3 | 0 | 0 |
| | Sum of objective substance and intermediates | | 96.0 | 96.0 | 95.5 | 95.5 | 97.8 | 97.7 | 97.4 | 97.3 | 96.8 | 96.8 |
| | Undesirable by-products | HCFC-133a | 1.1 | 1.1 | 0.9 | 0.9 | 0.9 | 0.9 | 0.7 | 0.7 | 0.9 | 0.9 |
| | | CFC-115 | 1.8 | 1.7 | 2.1 | 2 | 0.9 | 0.7 | 0.2 | 0.1 | 1.3 | 1.3 |

TABLE 1-continued

|  | Example 1 |  | Example 2 |  | Example 3 |  | Example 4 |  | Example 5 |  |
|---|---|---|---|---|---|---|---|---|---|---|
| CFC-114a | 0.7 | 0.8 | 0.9 | 1 | 0.2 | 0.5 | 0.5 | 0.6 | 0.6 | 0.6 |
| CFC-113a | 0 | 0 | 0 | 0 | 0 | 0 | 1.0 | 1.1 | 0 | 0 |
| HFC-23 | 0.2 | 0.2 | 0.3 | 0.3 | 0.1 | 0.1 | 0.1 | 0.1 | 0.2 | 0.2 |
| $CO_2$ | 0.2 | 0.2 | 0.3 | 0.3 | 0.1 | 0.1 | 0.1 | 0.1 | 0.2 | 0.2 |
| Sum of by-products | 4.0 | 4.0 | 4.5 | 4.5 | 2.2 | 2.3 | 2.6 | 2.7 | 3.2 | 3.2 |

Referring to Table 1, it was found that, according to Examples 1 to 5, the very high conversion ratio of PCE and the very high selectivities of the objective substance and the intermediates (particularly, high selectivity of HFC-125) as well as the low selectivity of the undesirable by-products were maintained over a long period of time, for example, more than 750 hours, still more than 1,000 hours, or further more than 2,000 hours. This suggests that the method of the present invention is preferred as the method for producing HFC-125.

Comparative Example 1

The same procedures were conducted as in Example 1, except that the packed amount of the catalyst was 66.0 g, the tubular reactor was maintained at about 0.15 MPa and 350° C., the feeding amount of HF was 378 cc/min, and the feeding amount of PCE was 18 cc/min, so that the molar ratio of HF to PCE was 21, and oxygen was not fed, and the contact time was 10 seconds. The results of analysis performed 49 hours and 611 hours after the start of the reaction are shown in Table 2.

Comparative Example 2

The same procedures were conducted as in Comparative Example 1, except that the tubular reactor was maintained at 0.1 MPa and 346° C., oxygen was fed simultaneously with PCE, and the feeding amount of oxygen was 0.036 cc/min, so that the feeding amount of oxygen with respect to PCE was 0.2% by mole. The contact time was 10 seconds. The results of analysis performed 74 hours and 691 hours after the start of the reaction are shown in Table 2.

Comparative Example 3

The same procedures were conducted as in Comparative Example 1, except that the tubular reactor was maintained at 0.1 MPa and 355° C., oxygen was fed simultaneously with PCE, the feeding amount of oxygen was 0.36 cc/min, so that the feeding amount of oxygen with respect to PCE was 2.0% by mole. The contact time was 10 seconds. The results of analysis performed 74 hours and 701 hours after the start of the reaction are shown in Table 2.

Comparative Example 4

The same procedures were conducted as in Comparative Example 1, except that the tubular reactor was maintained at 0.1 MPa and 359° C., oxygen was fed simultaneously with PCE, the feeding amount of oxygen was 0.54 cc/min, so that the feeding amount of oxygen with respect to PCE was 3.0% by mole. The contact time was 10 seconds. The results of analysis performed 73 hours and 673 hours after the start of the reaction are shown in Table 2.

TABLE 2

|  |  |  | Comparative Example 1 | | Comparative Example 2 | | Comparative Example 3 | | Comparative Example 4 | |
|---|---|---|---|---|---|---|---|---|---|---|
| After start of reaction (hours) | | | 49 | 611 | 74 | 691 | 74 | 701 | 73 | 673 |
| Conversion ratio of PCE (%) | | | 99.9 | 83.6 | 99.8 | 88.3 | 96.8 | 93.2 | 96.0 | 92.5 |
| Selectivity (% by mole) | Objective substance | HFC-125 | 86.5 | 51.6 | 84.9 | 56.9 | 75.5 | 71.4 | 70.5 | 64.0 |
| | Intermediates | HCFC-124 HCFC-124a | 7.6 | 24.3 | 8.4 | 27.1 | 12.6 | 14.9 | 13.0 | 16.1 |
| | | HCFC-123 HCFC-123a | 4.1 | 20.5 | 4.4 | 11.0 | 4.9 | 5.6 | 6.5 | 8.1 |
| | | HCFC-122 | 0 | 1.4 | 0 | 2.2 | 0 | 0.1 | 0.1 | 0.3 |
| | | CFC-1111 | 0 | 0.1 | 0 | 0.2 | 0.2 | 0.7 | 0.9 | 1.7 |
| | | CFC-1112a | 0 | 0 | 0 | 0 | 0 | 0.1 | 0.1 | 0.1 |
| | Sum of objective substance and intermediates | | 98.2 | 97.9 | 97.7 | 97.4 | 93.2 | 92.8 | 91.1 | 90.3 |
| | Undesirable by-products | HCFC-133a | 1.0 | 1.1 | 1.0 | 1.1 | 1.1 | 1.1 | 1.3 | 1.3 |
| | | CFC-115 | 0.3 | 0.2 | 0.6 | 0.4 | 3.5 | 3.3 | 4.5 | 3.9 |
| | | CFC-114a | 0.3 | 0.5 | 0.5 | 0.8 | 1.4 | 1.9 | 1.9 | 3.2 |
| | | CFC-113a | 0 | 0.1 | 0 | 0.1 | 0 | 0.1 | 0 | 0.1 |
| | | HFC-23 | 0.1 | 0.1 | 0.1 | 0.1 | 0.4 | 0.4 | 0.6 | 0.6 |
| | | $CO_2$ | 0.1 | 0.1 | 0.1 | 0.1 | 0.4 | 0.4 | 0.6 | 0.6 |
| | Sum of by-products | | 1.8 | 2.1 | 2.3 | 2.6 | 6.8 | 7.2 | 8.9 | 9.7 |

Referring to Table 2, in Comparative Example 1 where oxygen was not fed and Comparative Example 2 where the feeding amount of oxygen with respect to PCE was 0.2% by mole, the conversion ratio of PCE decreased to the order of 80% within about 700 hours after the start of the reaction. Therefore, it is understood that, when the feeding amount of oxygen with respect to PCE is 0-0.2%, the conversion ratio of PCE drastically decreases with the passage of the reaction time, and thus the catalytic activity cannot be maintained over a long period of time.

In Comparative Examples 3 and 4 where the feeding amounts of oxygen with respect to PCE were respectively 2.0% by mole and 3.0% by mole, the conversion ratio of PCE decreased to the value of about 92-93% within about 700 hours after the start of the reaction. Further in Comparative Examples 3 and 4, the selectivities of the by-products ware high. Therefore, it is understood that, when the feeding amount of oxygen with respect to PCE is 2.0% or more, the effect of suppressing deterioration of the catalyst is not enhanced, but the catalytic activity decreases and also the amount of the by-products increases.

INDUSTRIAL APPLICABILITY

According to the present invention, pentafluoroethane can be produced, which can be used, for example, as refrigerants, mixed refrigerants, blowing agents and propellants.

The invention claimed is:

1. A method for producing pentafluoroethane wherein tetrachloroethylene is reacted with HF in a gas phase in the presence of a catalyst to obtain pentafluoroethane, wherein chromium oxyfluoride is disposed in a reactor as the catalyst, oxygen is fed into the reactor together with tetrachloroethylene and HF at an amount of 0.4-1.8% by mole with respect to tetrachloroethylene, and wherein tetrachloroethylene and HF are fed into the reactor at a molar ratio of HF to tetrachloroethylene of not smaller than 20.

2. The method according to claim 1, wherein the reaction is carried out at a temperature of 310-380° C.

3. The method according to claim 1, wherein a fraction comprising pentafluoroethane and hydrogen chloride is separated from a reaction mixture which has been obtained from the reactor, and all of a remainder thereof is returned to the reactor.

4. The method according to claim 1 wherein the tetrachloroethylene and HF are fed into the reactor at a molar ratio of HF to tetrachloroethylene of 20-30.

* * * * *